(12) United States Patent
Alkayali

(10) Patent No.: US 10,287,339 B2
(45) Date of Patent: May 14, 2019

(54) HYDROLYZED JELLYFISH COLLAGEN TYPES I, II, AND V AND USE THEREOF

(71) Applicant: Ahmad Alkayali, Pauma Valley, CA (US)

(72) Inventor: Ahmad Alkayali, Pauma Valley, CA (US)

( * ) Notice: Subject to any disclaimer, the term of this patent is extended or adjusted under 35 U.S.C. 154(b) by 0 days.

(21) Appl. No.: 15/439,094

(22) Filed: Feb. 22, 2017

(65) Prior Publication Data

US 2018/0237498 A1 Aug. 23, 2018

(51) Int. Cl.
*A61K 38/01* (2006.01)
*C07K 14/78* (2006.01)
*A61K 8/00* (2006.01)
*A61K 35/614* (2015.01)
*A61K 38/00* (2006.01)

(52) U.S. Cl.
CPC .............. *C07K 14/78* (2013.01); *A61K 8/00* (2013.01); *A61K 35/614* (2013.01); *A61K 38/014* (2013.01); *A61K 38/00* (2013.01)

(58) Field of Classification Search
None
See application file for complete search history.

*Primary Examiner* — Lianko G Garyu
(74) *Attorney, Agent, or Firm* — MU P.C.

(57) ABSTRACT

Hydrolyzed collagen types I, II, and V powder compositions, method of preparing the compositions, and use of the compositions in treating a variety of ailments. The compositions are topically or orally administered to an individual at a daily dosage between 1500 mg and 2000 mg.

9 Claims, 1 Drawing Sheet

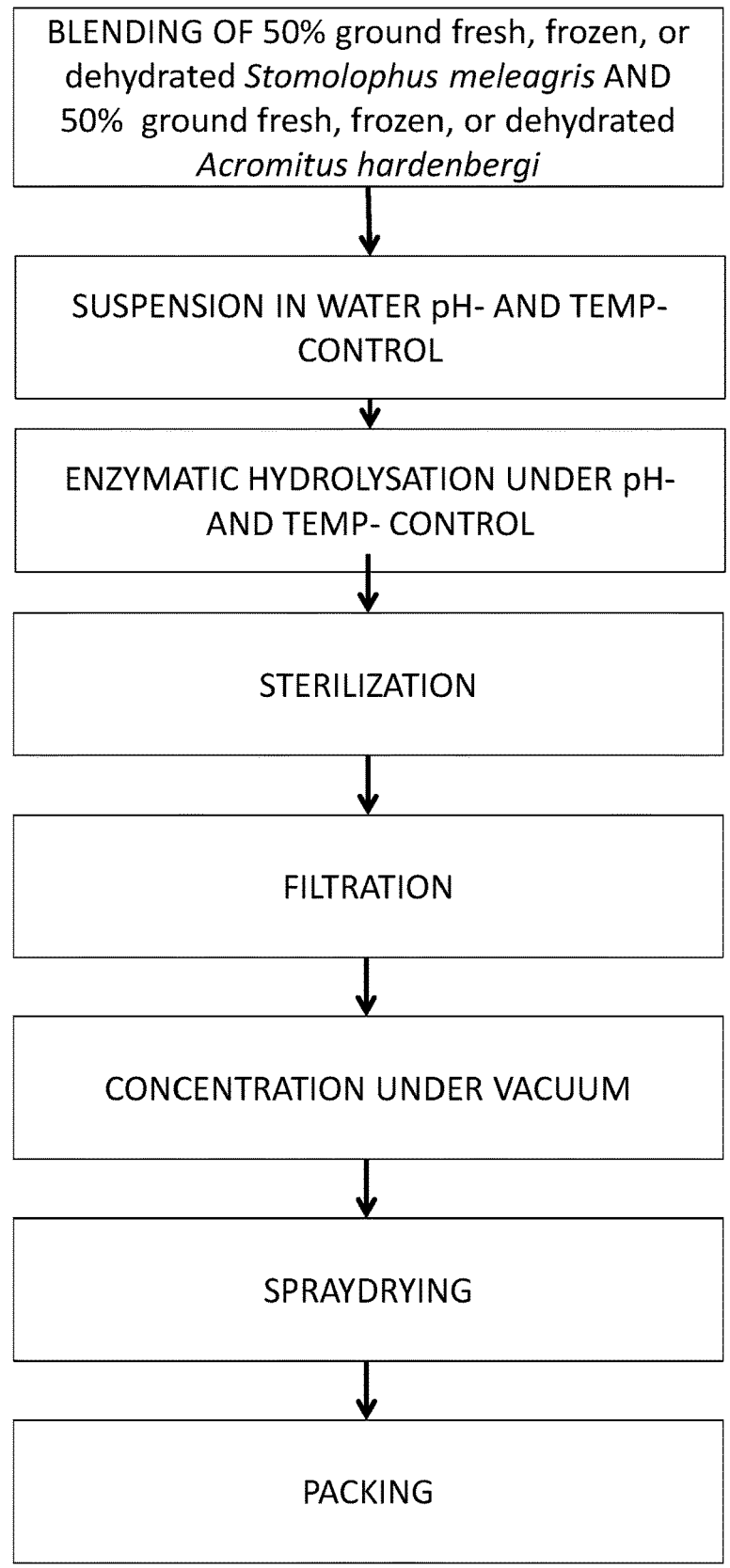

HYDROLYZED JELLYFISH COLLAGEN TYPES I, II, AND V AND USE THEREOF

BACKGROUND OF THE INVENTION

1. Field of Invention

The present invention relates to a method of preparation for hydrolyzed collagen type I, II, and V and its use as a therapeutic agent and nutritional supplement.

2. Description of Related Art

Collagen is a complex structural protein which provides strength and flexibility to skin, hair, and nails. Collagen is a major component of muscles, tendons, cartilage, ligaments, joints, and blood vessels. Hydrolyzed coastal jellyfish collagen is extracted from two species of edible jellyfish. The two species, *Stomolophus meleagris* and *Acromitus hardenbergi*, contain the highest amount of amino acid collagen types I, II, and V. Type I is primarily found in skin and tendons while type II is primarily found in articular cartilage. Cartilage is unusual in that it has a high proportion of glycine and proline residues. Specifically 4-hydroxyproline and 5-hydroxylysine are found in very few other protein sources, adding benefit to the intake of exogenous collagen.

U.S. Pat. No. 4,804,745 Koepff et al. discloses agents containing collagen peptides produced by enzymatic hydrolysis for the treatment of degenerative joint diseases. These peptides can be obtained from animal skin, animal bones, and other purified connective tissues. Peptides of this nature have an average molecular weight of 30 to 45 kilodaltons.

U.S. Pat. No. 5,399,347 Trentham et al. and Trentham et al. (science 261:1727-1729, 1993) disclose the effective treatment of rheumatoid arthritis with water-soluble whole chicken collagen type II or biologically active peptides derived therefrom.

U.S. Pat. No. 5,364,845 Henderson discloses a therapeutic composition and method for the protection, treatment, and repair of connective tissue in mammals comprising glucosamine, chondroitin sulfate, and manganese ascorbate.

U.S. Pat. No. 5,587,363 to Henderson discloses a therapeutic composition and method for the protection, treatment, and repair of connective tissue in mammals including aminosugars and glycosaminoglycans.

U.S. Pat. No. 6,025,327 to Alkayali et al. discloses a composition of hydrolyzed collage type II and a method of preparation thereof. The invention is useful in treating cartilage defects.

U.S. Pat. No. 6,838,440 to Stiles et al. discloses a composition and method of preparation for a desiccated avian sternal cartilage powder and specifically its use in treating arthritic joint cartilage diseases.

Several research studies on hydrolyzed jellyfish collagen have been conducted in vivo showing positive health benefits such as improved brain function, reversal of photoaging, fatigue reduction, arthritis prevention, and reduced cellular oxidation. Further, collagen helps to stimulate the immune system and neurological activities.

Based on the foregoing, there is a need in the art for a new composition of collagens types I, II, and V that may be utilized as a supplement, prophylactic, or treatment for a wide range of conditions. The composition should be available for use in a variety of forms for topical or oral administration.

SUMMARY OF THE INVENTION

A jellyfish-derived material comprises hydrolyzed collagen types I, II, and V having an average molecular weight of 4 kilodaltons and 20 kilodaltons. Preferentially, the hydrolyzed collagen is sourced from *Stomolophus meleagris* and *Acromitus hardenbergi*. The hydrolyzed collagen is formulated into a delivery vector comprising one or more gelatin capsules, one or more aqueous solutions, one or more oil suspensions, one or more elixirs, one or more tables, and a powder.

A method for providing collagen types I, II, and V as a supplement includes administering to an individual a daily dose of a hydrolyzed collagen types I, II, and V, wherein the preferred daily dose is between 1500 mg and 2000 mg. The supplement may be formulated as a topical cream, orally administered tablet, or likewise vector.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the ensuing descriptions taken in connection with the accompanying drawings briefly described as follows.

FIG. 1 is a schematic diagram of the process for preparing the hydrolyzed jellyfish collagen powder, according to an embodiment of the present invention.

DETAILED DESCRIPTION OF PREFERRED EMBODIMENTS

Preferred embodiments of the present invention and their advantages may be understood by referring to FIG. 1, wherein like reference numerals refer to like elements.

In general, the invention described herein refers to a composition with hydrolyzed collagen types I, II and V sourced from jellyfish, a method for preparing the composition, and use of the composition. The method of production involves grinding fresh, frozen, or dehydrated jellyfish. In a preferred embodiment, the jellyfish are *Stomolophus meleagris* and *Acromitus hardenbergi*. These species contain the highest levels of collagen type I, II, and V. The bell and oral arms are isolated from the jellyfish wherein high concentrations of collages types I, II, and V exist. Prior art involves cutting and separating meat and bone from the carcass of an animal such as a chicken. Jellyfish are a preferred source as they do not contain bone, brain, or a heart. They are comprised of 5% solid matter and 95% water making the isolation of proteins a more simple process. Standard GMP processes are used throughout the entire process to produce a powdered collagen types I, II, and V supplement for oral, topical, or likewise administration. The powder will be a blend of amino acids present The production of hydrolyzed jellyfish collagen in powdered form is shown in FIG. 1. In step 5, fresh, frozen, or dehydrated jellyfish are sourced and the bell and oral arms are separated. A final composition of 50% *Stomolophus meleagris* and 50% *Acromitus hardenbergi* is processed by grinding each of the components together. In step 10, the ground jellyfish are suspended and incubated in an aqueous solution, preferably water, for 24 hours at a temperature of 35° C. at a pH between about 4 and 8. The grinding of the jellyfish allows for the salt removal and washing process to be more efficient. The suspension and incubation period is repeated three times to remove salt from the suspension. In step 15, the water is removed from the suspension leaving the jellyfish particulates behind for purification. Enzymatic hydrolysation is obtained by incubating the jellyfish with one or more proteases under pH and temperature control to form a hydrolysate. The overall range of molecular weight is between 4 kilodaltons and 20 kilodaltons. In a preferred embodiment, the molecular weight of the product is between 15 kilodaltons and 20 kilodaltons. The protease may include pancreatin, papain, ficin, or bromelain and are preferentially sourced sustainably. The pH will depend on the optimum activation pH of the specific enzyme used for the hydrolysation as known in the art. In a preferred embodiment, the protease enzyme pancreatin is used at a pH between 7.5 and 8. At this pH the protease is effective at a temperature between 45° C. and 50° C. At this pH and temperature range an incubation period of 12 hours is used. In step 20, the hydrolysate is sterilized for 30 minutes at a temperature between 95° C. and 105° C. In another preferred embodiment, the protease enzyme papain is used at pH between 6 and 6.5. At this pH, the papain is effective at a temperature between 52° C. and 57° C. At this pH and temperature range, an incubation period of 8 hours is used. In steps 25 to 40, the sterilized hydrolysate is filtered through diatomaceous earth, concentrated under vacuum, dried to form the powder, and packaged for retail, consumption, storage, or otherwise. In an alternative embodiment, other methods of filtration, such as vacuum filtration may be used. In a preferred embodiment, the vacuum concentrated hydrolysate is spray dried through a size 56 pressure nozzle into a heat tunnel. The final particle size and mesh are adjusted to 0.46 g/cc, which will result in a fine powder. The fine powder is comprised of collagen types I, II, and V, as well as a blend of other amino acids present in the jellyfish oral arms and bell. The powder may then be packed in a 40 kg drum having a plastic bag liner. This process yields a water soluble product.

The amino acid composition of the final hydrolysate of types I, II, and V collagen is shown below in Table 1. The amino acid composition of the hydrolysate may differ substantially from typical collagens. The composition and molecular weights of the peptides allow for an increase in the bio-assimilation of the peptides. Table 2 shows the mineral content of the final composition. In a preferred embodiment, the final composition is composed of 30% to 40% collagen peptides, and 30% to 35% minerals such as calcium, potassium, sodium, iron, zinc, sulfur, magnesium, copper, phosphorous, manganese, and chloride.

TABLE 1

| | |
|---|---|
| ASPARTIC ACID | 2.99% |
| THREONINE | 2.32% |
| SERINE | 1.56% |
| GLUTAMIC ACID | 5.77% |
| PROLINE | 3.72% |
| GLYCINE | 6.79% |
| ALANINE | 3.64% |
| CYSTINE | 0.36% |
| VALINE | 1.09% |
| METHIONINE | 0.47% |
| ISOLEUCINE | 1.41% |
| LEUCINE | 1.94% |
| TYROSINE | 0.76% |
| PHENYLALANINE | 0.52% |
| LYSINE (TOTAL) | 1.87% |
| HISTIDINE | 0.24% |
| ARGININE | 2.84% |
| TRYPTOPHAN | 0.14% |
| TOTAL | 38.43% |

TABLE 2

| | |
|---|---|
| CALCIUM | 0.43% |
| POTASSIUM | 0.435% |
| SODIUM | 10.6% |
| IRON | 0.00284% |
| ZINC | 0.0035% |
| SULFUR | 2.22% |
| MAGNESIUM | 1.08% |
| COPPER | 0.0004% |
| PHOSPHOROUS | 0.155% |
| MANGANESE | 0.0% |
| CHLORIDE | 17.1% |
| TOTAL | 32.02674% |

In an embodiment, the average molecular weight of the product is between 15 kilodaltons and 20 kilodaltons. In a preferred embodiment, the final moisture content is between 2% and 5%. The final product is high in mucopolysaccharides, particularly chondroitin sulfate and glucosamine sulfate as shown in Table 3.

TABLE 3

| | |
|---|---|
| CHONDROITIN SULFATE | 10.59% |
| HYALURONIC ACID | 3.21% |
| MUCOPOLYSACCARIDE | 29.4% |
| GLUCOSOMINE | 0.19% |
| TOTAL | 38.43% |

When taken orally, research shown that hydrolyzed jellyfish collagen is beneficial in promoting brain function in age related neurological diseases. Oral administration may include oral, enteral, or intragastic administration. Several other research studies have shows benefits in reversing photo-aging, reducing fatigue, preventing arthritis, and reducing cell oxidation. Furthermore, the immune system is stimulated along with an increase in neurological activities. The targeted molecular weight range of 4 kilodaltons to 20 kilodaltons allows for the human body to easily assimilate the essential nutrient presents in the composition.

Type I collagen is the most abundant collagen in the human body. It is used in treating conditions of the bone and skin. Type II collagen is found in joint cartilage. Its oral ingestions appears to reduce autoimmunity resulting in reduced inflammation in instances of osteoarthritis and rheumatism. Other forms of connective tissue disorders have been greatly benefitted by type II collagen. Type V collagen has been associated with Ehlers-Danlos syndrome as well as other genetic and non-genetic connective tissue disorders. Various types of collagen have been found to reduce wrinkles, support re-growth of joint tissue, relieve joint pain, prevent osteoporosis, reduce cellulite, prevent stretch marks, aid in weight loss, detoxify the liver, repair leaky gut syndrome, support healthy hair growth, grow stronger nails, support healthy teeth, balance hormones, alleviate anxiety, promote restful sleep, prevent atherosclerosis, increase brain function, among many more benefits. Supplementing hydrolyzed collagen types I, II, and V can effectively be accomplished by oral ingestion or topical application depending on the desired result.

The composition may be taken as a nutritional supplement, prophylactic agent, or therapeutic. Oral administration may be accomplished by taking a powder, tablet, oil emulsion, aqueous or oil suspension, hard or soft capsule, syrup, tincture, or elixir. Each of these embodiments may be formed by a method known in the art for the manufacture of pharmaceutical, nutraceutical, or supplemental agents. The final product may contain artificial or natural sweeteners, flavoring agents, coloring agents, binding agents, thickening agents, emulsifiers, and preservatives. Any of these ingredients, and the combination thereof may increase the palatability of the composition. Binding agents may include starch, gelatin and acacia. Granulating and disintegrating agents may include corn starch and alginic acid. Lubricating agents may also be included including magnesium stearate, stearic acid, and talc. Furthermore, adjuvants as known in the art may be added to increase the bio-availability of the composition. Further, inert excipients may be used as known in the art. Excipients may include calcium carbonate, sodium carbonate, lactose, calcium phosphate, and sodium phosphate. If a tablet form is used, the tablets may be instantized, or time buffered by adjusting the coating of the tablet. Time buffering materials such as wax, glyceryl monostearate, or glyceryl distearate may be used. In further embodiment, enteric coatings may be used. In further embodiments, the composition may take forms as found in the cosmetic industry, such as facial creams, body lotions, lip sticks, and other skin topical treatments.

In oral use formulations, mixing the active ingredients of the composition with an inert solid diluent may produce hard capsules as known in the art. The inert solid diluent may include calcium carbonate, calcium phosphate, and kaolin. Soft gel formulations may include mixing the active ingredients of the composition with water or an oil medium.

Aqueous suspensions may be produced as known in the art through the utilization of suspending agents, dispersing agents, wetting agents, among others known in the art. Sweetening agents may be used as known in the art, including sucrose or saccharin.

Oil suspensions may be formulated by suspending the active ingredients of the composition in one or a combination of oils known in the art. Oil suspensions may contain a thickening agent such as waxes, hard paraffin, or cetyl alcohol. Oils used may be vegetable oil, coconut oil, arachis oil, mineral oil, or others.

Syrups and elixirs may be formulated with sweeting agents, demulcents, preservatives, flavoring agents, and coloring agents as known in the art.

Research studies show that ascorbic acid found in fruit juices promotes the formation of connective tissues when combined with hydrolyzed collagen powder. For this reason, a preferred embodiment involves combining the hydrolyzed collagen powder with an acid fruit juice prior to oral administration. Further, the fruit juice may be foregone by the user of powdered ascorbic acid mixed with the active ingredients of the composition in a tablet.

In a preferred embodiment, the active ingredients are formulated in one or more of the above-mentioned embodiments. The composition is administered orally as a nutritional supplement. The hydrolyzed collagen is administered at a daily dosage of 200 mg to 5000 mg. In a preferred embodiment, the effective daily dose is between 1500 mg and 2000 mg. In another preferred embodiment, the hydrolyzed collagen is taken on an empty stomach with a beverage containing ascorbic acid (vitamin C). In a preferred embodiment, the hydrolyzed collagen is mixed with the ascorbic acid containing beverage prior to administration of the mixture.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

I claim:

1. A Jellyfish-derived material comprising:
   a. a hydrolyzed collagen compound, wherein the hydrolyzed collagen compound is defined by hydrolyzed collagen type I, hydrolyzed collagen type II, and hydrolyzed collagen type V, and wherein the hydrolyzed collagen compound has an average molecular weight between 4 kilodaltons and 20 kilodaltons.

2. The material of claim 1, wherein the jellyfish-derived material is derived from a group of jellyfish species consisting of: *Stomolophus meleagris, Acromitus hardenbergi*, and combination thereof.

3. The material of claim 1, and wherein the jellyfish-derived material is a mixture comprising 30-40% of the hydrolyzed collagen compound, 30-35% minerals, the minerals comprising calcium, potassium, sodium, iron, zinc, sulfur, magnesium, copper, phosphors, manganese, and chloride, and 25-40% materials, the materials comprising chondroitin, hyaluronic acid, mucopolysaccarides, and glucosamine.

4. The material of claim 3, wherein the jellyfish-derived material is formulated into a delivery vector comprising one or more gelatin capsules.

5. The material of claim 3, wherein the jellyfish-derived material is formulated into a delivery vector comprising one or more aqueous suspensions.

6. The material of claim 3, wherein the jellyfish-derived material is formulated into a delivery vector comprising one or more oil suspensions.

7. The material of claim 3, wherein the jellyfish-derived material is formulated into a delivery vector comprising one or more elixirs.

8. The material of claim 3, wherein the jellyfish-derived material is formulated into a delivery vector comprising one or more tablets.

9. The material of claim 3 wherein the jellyfish-derived material is formulated into a delivery vector comprising a powder.

* * * * *